(12) United States Patent
Tranvouez et al.

(10) Patent No.: US 10,234,698 B2
(45) Date of Patent: Mar. 19, 2019

(54) METHOD FOR DETERMINING A LENS DESIGN OF AN OPTICAL LENS ADAPTED TO A WEARER

(71) Applicant: Essilor International, Charenton-le-Pont (FR)

(72) Inventors: Delphine Tranvouez, Charenton-le-Pont (FR); Isabelle Poulain, Charenton-le-Pont (FR); Gildas Marin, Charenton-le-Pont (FR); Laurent Calixte, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/517,379

(22) PCT Filed: Sep. 22, 2015

(86) PCT No.: PCT/EP2015/071796
§ 371 (c)(1),
(2) Date: Apr. 6, 2017

(87) PCT Pub. No.: WO2016/055265
PCT Pub. Date: Apr. 14, 2016

(65) Prior Publication Data
US 2017/0299888 A1    Oct. 19, 2017

(30) Foreign Application Priority Data
Oct. 8, 2014    (EP) .................................... 14306579

(51) Int. Cl.
*G02C 7/02* (2006.01)
*A61B 3/113* (2006.01)
*G02C 7/06* (2006.01)

(52) U.S. Cl.
CPC .............. *G02C 7/024* (2013.01); *A61B 3/113* (2013.01); *G02C 7/02* (2013.01); *G02C 7/027* (2013.01);
(Continued)

(58) Field of Classification Search
CPC .......... G02C 7/024; G02C 7/02; G02C 7/027; G02C 7/028; G02C 7/061; G02C 2202/08; A61B 3/113
(Continued)

(56) References Cited

U.S. PATENT DOCUMENTS 5,892,570 A * 4/1999 Stevens ................. A61B 3/024
351/222
8,465,153 B1 * 6/2013 Bruun-Jensen .......... A61B 3/08
351/200
(Continued)

FOREIGN PATENT DOCUMENTS

DE    102007015908 A1    10/2008
WO    2014/037482 A2    3/2014

OTHER PUBLICATIONS

International Search Report and Written Opinion dated Nov. 18, 2015, in PCT/EP2015/071796, filed Sep. 22, 2015.

*Primary Examiner* — William R Alexander
(74) *Attorney, Agent, or Firm* — Oblon, McClelland, Maier & Neustadt, L.L.P.

(57) ABSTRACT

A method, implemented by a computer, for determining a lens design of an optical lens adapted to a wearer, the method including: providing a wearer parameter; a lens design determining, during which the lens design of the optical lens adapted to the wearer is determined based at least on the wearer parameters. The wearer parameters include at least optical distortion sensitivity data representative of sensitivity of the wearer to optical distortions.

16 Claims, 2 Drawing Sheets

(52) U.S. Cl.
CPC .............. *G02C 7/028* (2013.01); *G02C 7/061* (2013.01); *G02C 2202/08* (2013.01)

(58) Field of Classification Search
USPC ..................................................... 351/159.74
See application file for complete search history.

(56) References Cited

U.S. PATENT DOCUMENTS

| | | | | |
|---|---|---|---|---|
| 8,985,767 | B2* | 3/2015 | Spratt | G02C 7/027 |
| | | | | 351/159.06 |
| 9,131,838 | B1* | 9/2015 | Bruun-Jensen | A61B 3/005 |
| 9,772,513 | B2* | 9/2017 | Qi | G02C 13/00 |
| 9,910,294 | B2* | 3/2018 | Altheimer | G02C 7/028 |
| 2010/0198515 | A1 | 8/2010 | Becken et al. | |
| 2012/0026183 | A1 | 2/2012 | Qi et al. | |
| 2014/0268007 | A1* | 9/2014 | Ben-Shahar | G02C 5/001 |
| | | | | 351/110 |
| 2014/0268060 | A1 | 9/2014 | Lee et al. | |
| 2015/0219924 | A1 | 8/2015 | Moine et al. | |

* cited by examiner

METHOD FOR DETERMINING A LENS DESIGN OF AN OPTICAL LENS ADAPTED TO A WEARER

The invention relates to a method for determining a lens design of an optical lens adapted to a wearer, a corresponding lens design determining system and a computer program product comprising one or more stored sequence of instruction that is accessible to a processor and which, when executed by the processor, causes the processor to carry out the steps of the methods according to the invention.

Methods for customizing vision correction includes measuring data of a wearer, determining the lens parameters and offering to the wearer the best adapted lens design among a plurality of model lenses.

Progressive addition lenses (PAL) generate aberrations blur that in particular reduce the field of view and distortion that creates for exemple the well known swim effect. The design is necessarily a compromise between these aberrations.

Now, it is also known for some design features of a progressive lens to be adapted according to a wearer for whom the lens is designed, in particular in order to reduce the time that could be required for the wearer to become accustomed to this progressive lens. Such an adaptation of the lens is referred to as 'customization' of the design feature.

For example, a device has been developed and commercialized by the applicant under the trademark Varilux Ipseo in order to improve customizing vision correction. This device is used to measure the head-eye movement ratio, which corresponds to a visual imprint of the particular wearer, and personalized progressive lenses are manufactured after processing the data to create a design which matches physiological characteristics of the wearer.

Indeed, an individual test makes it possible to assign to each individual wearer a coefficient that qualifies his propensity to rather move the head or rather move the eyes (head mover/eye mover). This behavioral coefficient presides over calculation of the best suited design. Thus, for example, for a wearer who tends to move the eyes rather than the head, a design having a fairly wide sharp vision field will be chosen, in other words having a high power gradient. Such design is called a hard design. Nevertheless, such design generates more distortions. As against this, for a wearer who rather tends to move more the head than the eyes, soft progression at the periphery will be chosen to avoid an impression of swaying. Such design having a smoother power gradient is called a soft design.

There is also an increasing need for customizing progressive addition lenses to the wearer's habits or to his specific needs, such as for example, customizing lenses for car driving or sport training or office working including computer use or other everyday life needs, or also, when the wearer choices a particular frame which geometry is not adapted to standard progressive addition lenses.

While it is clear that the eye-head behavior or activity impacts the perception of distortions (distortions of a given lens are especially seen when the wearer will move the head), it is not an intrinsic sensitivity to distortions of the wearer (although the two may be linked to the end). For example, two wearers with the same eye-head coefficient ($COT_1=COT_2$) may have different sensitivities to distortions. It is better to propose a smoother design to the wearer having a higher sensitivity. Conversely, a harder design should be proposed to the wearer having a less sensitivity.

So, the best compromise between blurred aberrations and distortion generated by PAL is not always the same depending on the wearer.

The distortions can be particularly troublesome in particular during the period of adaptation, and/or with the aging of the sensory and cognitive system. It is therefore necessary to customize the design for each wearer, taking into account priority of its sensitivity to distortions in order to facilitate its adaptation to progressive addition lenses.

One object of the present invention is to provide a method for determining a lens design of an optical lens best adapted to a wearer in order to reduce the time that could be required for the wearer to become accustomed to these progressive addition lenses.

To this end, the invention proposes a method, implemented by computer means, for determining a lens design of an optical lens adapted to a wearer according to the invention comprises:
- a wearer parameter providing step, during which wearer parameters are provided,
- a lens design determining step, during which the lens design of the optical lens adapted to the wearer is determined based at least on the wearer parameters, wherein the wearer parameters comprise at least optical distortion sensitivity data representative of the sensitivity of the wearer to optical distortions.

Advantageously, the method according to the invention allows determining a lens design which takes account of one or more parameters characterizing the sensitivity of the wearer to optical distortions for the selection or customization lens design or geometry of the front face of the lens.

Consequently, thanks to the invention the wearer is accustomed more quickly to its new lens.

According to further embodiments which can be considered alone or in combination:
- each optical distortion sensitivity data is compared to a scale to define an optical distortion sensitivity index; and/or
- the wearer parameters further comprise, in addition to prescription data, ophthalmic parameters relating to the ophthalmic requirements of the wearer; and/or
- during the determination step, the lens design is calculated based at least on the optical distortion sensitivity data; and/or
- during the determination step the lens design is selected in a list of lens designs, the selection being based at least on the optical distortion sensitivity data; and/or
- the lens design comprises at least the dioptric lens design; and/or
- the lens design comprises geometrical parameters of the optical lens; and/or
- the method further comprising an optical distortion sensitivity data measurement step during which the optical distortion sensitivity data of the wearer are measured; and/or
- the optical distortion sensitivity data are measured upon a perception test or a discomfort measurement test carried out on the wearer; and/or
- during the optical distortion sensitivity data measurement step optical distortion patterns are presented to the wearer; and/or
- the optical distortion patterns comprise dynamic optical distortion patterns; and/or
- the optical distortion sensitivity data are measured in specific gazing directions; and/or
- the optical distortion sensitivity data are measured in at least a specific part of the field of vision.

The invention further relates to a method of providing an optical lens adapted to a wearer, the method comprising:
- a lens design determining step according to any of the preceding claims,
- an optical lens manufacturing step during which an optical lens having the determined lens design is manufactured.

According to a further aspect, the invention relates to a lens design determining system for determining lens design adapted to a wearer, the system comprising:
- receiving means adapted to receive wearer parameter comprising at least optical distortion sensitivity data representative of the sensitivity of the wearer to optical distortion,
- determining means adapted to determine the lens design of the optical lens adapted to the wearer based at least on the wearer parameters.

The invention further relates to a computer program product comprising one or more stored sequences of instructions that are accessible to a processor and which, when executed by the processor, causes the processor to carry out the steps of the methods according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

Embodiments of the invention will now be described, by way of example only, and with reference to the following drawings in which.

Figure 1:
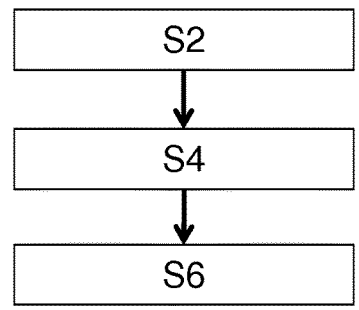
FIG. 1 is an illustration of a chart-flow of an embodiment of the method according to the invention.

As represented on FIG. 1, the invention also relates to a method, implemented by computer means, for determining a lens design of an optical lens adapted to a wearer. The method comprises at least:
- a wearer parameter providing step S4, during which wearer parameters are provided, and
- a lens design determining step S6, during which the lens design of the optical lens adapted to the wearer is determined based at least on the wearer parameters.

Of course, the wearer parameters comprise at least prescription data representing the prescription of the wearer, for example sphere, cylinder, axis, an addition power and prism if necessary.

The wording "lens design" or "optical design" is a widely used wording known from the man skilled in the art in ophthalmic domain to designate the set of parameters allowing to define a dioptric function of an ophthalmic lens; each ophthalmic lens designer has its own designs, particularly for progressive ophthalmic lenses.

In the sense of the invention, an optical function corresponds to a function providing for each gaze direction the effect of the optical lens on the light ray passing through the optical lens.

The optical function may comprise a dioptric function, light absorption, polarizing capability, reinforcement of contrast capacity, etc. . . . .

The dioptric function corresponds to the optical lens power (mean power, astigmatism etc. . . . ) as a function of the gaze direction.

As for an example, a progressive ophthalmic lens "design" results of an optimization of a progressive surface so as to restore a presbyope's ability to see clearly at all distances but also to optimally respect all physiological visual functions such as foveal vision, extra-foveal vision, binocular vision and to minimize unwanted astigmatisms. For example, a progressive lens design comprises:
- a power profile along the main gaze directions (meridian line) used by the lens wearer during day life activities,
- distributions of powers (mean power, astigmatism, . . . ) on the sides of the lens, that is to say away from the main gaze directions.

These optical characteristics are part of the "designs" defined and calculated by ophthalmic lens designers and that are provided with the progressive lenses.

According to the invention, the wearer parameters comprise at least optical distortion sensitivity data representative of the sensitivity of the wearer to optical distortions.

In the sense of the invention, optical distortion is an aberration affecting the geometry of the visual scene. It may be aberration produced by ophthalmic lens (but not including the modification of sharpness), either unifocal or progressive lens, or part of it. For example we can use specific combination of some terms of the decomposition of it using a classical polynomial decomposition like Zernike, monome, Tchebitchev polynomial for example. It may be more complex deformation (linear, non-linear, local or global). It may be dynamic distortion referring to aberration changing in time.

Moreover the wearer parameters may comprise, in addition to prescription data, ophthalmic parameters relating to the ophthalmic requirement of the wearer in order to better suit to the wearer's need, for example parameters of the spectacle frame chosen by the wearer, postural parameters of the wearer of the spectacle frame in a vision posture, pantoscopic angle of each lens when worn, the height of the eyes of the wearer relative to the lower edge of the lens . . . .

According to a preferred embodiment of the invention, the lens design comprises at least the dioptric lens design and/or geometrical parameters of the optical lens.

Sensitivity of the wearer to optical distortions can be detected subjectively or objectively, for example thanks to questionnaires or perception test. Such questionnaires may include questions like "difficulty climbing stairs", or "perception to deformation of the geometry", each question being associated to a sensitivity indicator graduated from 0 (no difficulty or no perception) to 5. In a perception test, the presentation of a visual stimulus allows us to measure a perceptual threshold associated to a sensitivity indicator, independently upon the wearer satisfaction.

This sensitivity to optical distortions is manifested as discomfort and/or a change of the perception of visual index (for example: curvatures), motor skills (for example: modification of eye-head coordination, postural oscillation) and/or sensorimotor loops (for example: change in response times) . . . . One or more of these indicators will provide a profile of wearer's sensitivity to distortions evaluated for example between 0 (insensitive) and 5 (very sensitive). The evaluated profile of wearer's sensitivity to distortions forms the optical distortion sensitivity data.

Preferably, the method according to the invention further comprises an optical distortion sensitivity data measurement step S2 during which the optical distortion sensitivity data of the wearer are measured.

The optical distortion sensitivity data may be measured directly by the presentation of optical distortions patterns to the wearer. The optical distortion patterns can comprise dynamic optical distortion patterns. For example, a grid or image can be displayed to the wearer and the deformation of the grid that a wearer would experiment wearing a real lens can be simulated, the deformation being obtained by gradually increasing the lens distortion. To determine sensitivity, the levels of distortion from which the wearer perceives distortions and/or from which distortion become bothersome are determined. The distortion can be simulated for example by taking existing designs lenses, with increasing distortion.

Preferably, each optical distortion sensitivity data is then compared to a scale to define an optical distortion sensitivity index. A sensitivity indices scale can be defined with respect to the responses of a sample of wearer for each design or pattern of distortion:

index equal to 5: no wearer detects or is disturbed by distortion, index equal to 2: 2/5 of the wearer detect or are disturbed by distortion, index equal to 0: 100% of wearer detect or are disturbed by distortion.

The sensitivity indices can then be defined for a particular wearer with respect to the previously defined scale:

index equal to 5: wearer detects or is disturbed by distortion on all designs, index equal to 2: wearer detects or is disturbed by distortion on 2/5 of the designs, index equal to 0: wearer never detects or is disturbed by distortion.

The optical distortion sensitivity data may be measured indirectly upon a perception test or a discomfort measurement test carried out on the wearer.

For example, the well-known Useful Field Of View (UFOV), a computer-administrated and scores test of visual attention developed by Visual Awareness Company can be used. A high score in UFOV test demonstrates greater sensitivity to peripheral visual field and hence to distortion. An intrinsic optical distortion sensitivity index (ISID) can be defined for example as the ratio between UFOV and UFOVmax multiplied by N, wherein N is typically equal to 5.

Furthermore, the optical distortion sensitivity data can be measured in specific gazing directions and/or in one or more specific parts of the field of vision of the wearer (central vision zone or peripheral vision zone) and/or in different part of the lens (nasal, temporal, monocular or binocular zone). For example, a grid or image can be displayed to the wearer and the deformation of the grid can be simulated, the deformation being obtained by gradually increasing the lens distortion only in the specific gazing directions and/or in one or more specific parts of the field of vision.

Moreover, the optical distortion sensitivity data can be measured for a specific activity or several different activities. Indeed, according to specific activities, the wearer may need to use different parts of the lens, and thus the sensitivity to the distortion can be especially valued in these zones. Moreover, some activities will require quantities and types of motion that generate quantities and types of distortion (for example dynamic or static, vertical curvature versus ground motion).

The intrinsic sensitivity means the absolute or relative sensitivity of a wearer with respect to a given (static or dynamic) pattern of distortion projected onto a given location of the retina (more or less peripheral vision).

It is possible to test optical distortion sensitivities for different distortions (multiple, static or dynamic patterns). Indeed it is known in particular that adaptation to distortions present in unifocal lenses, while important and can interfere with an unaccustomed wearer, is faster than adaptation to distortions present in progressive addition lenses, even though not larger than in unifocal lenses. Consequently, there are several types of distortions which the wearers adapt more or less easily, and that according to the sensitivities of the wearers. It may therefore be interesting to test several types of distortions to determine lenses that reduce those that appear the most troublesome about in daily activities.

In consequence, a specific intrinsic optical distortion sensitivity data can be measured for each specific distortion. A mathematical function of these specific intrinsic optical distortion sensitivity data can be calculated in order to form the intrinsic optical distortion sensitivity index (ISID).

The ISID can also be determined relatively for example by displaying a grid or image to the wearer, equipped with its current visual equipment and simulating a change in the deformation of the grid, the change of the deformation being obtained by a change in the distortion resulting by an increase or a decrease of the lens distortion.

In addition to the initial profile of intrinsic sensitivity to distortions of the wearer, other parameters can be taken into account to calculate an index of acceptance of distortions (IAD) such as the current optical equipment of the wearer, the level of satisfaction with the distortions, the age and change in vision correction.

For example, a wearer satisfied of its initial equipment is well-accustomed to the distortions of his equipment. This habit comes to weight the intrinsic optical distortion sensitivity index (ISID). The type, level and distribution of distortions of the initial equipment will be included in the index of acceptance of distortions (IAD). This is even truer that the wearer is old because it is more difficult to adapt to a change in distortion.

Thus, a low index of acceptance of distortions (IAD) means a low tolerance to distortions. On the contrary, a high index of acceptance of distortions indicates a high tolerance to distortions.

The IAD, ISID and the specific ISID will be sent for example from the optician to a lab. These indices are to be used to determine a lens design of an optical lens adapted to a wearer according to the invention. Of course, these indices can also be determined by the lab or a calculator during the determining of the lens from data sent by the optician. The measured data can also be sent to a cloud and the indices can thus be determined and sent again to an optician, a lab or a calculator.

According to the invention, during the determination step S6, the lens design is calculated based at least on the optical distortion sensitivity data and/or selected in a list of lens designs, the selection being based at least on the optical distortion sensitivity data.

Thus a soft lens design will be associated with low optical distortion sensitivity and respectively a hard design with high optical distortion sensitivity.

For example, the lens design can be selected to generate a level of optical distortion at or below the optical distortion sensitivity data provided in step S4.

A plurality N of lens design can be associated with a plurality of levels of optical distortion sensitivity: from a very soft lens design (lens design 1) corresponding to a very low optical distortion sensitivity to a very hard lens design (lens design N) corresponding to a very high optical distortion sensitivity.

According to another example, the lens design is calculated in order to minimize distortions of the lens design by using a regressive front face and a high base curve. In this case, it is possible to determine a lens design of an optical lens adapted to the wearer by only varying the distortion by acting on the front face. For example, a list of N front face designs can be calculated, each corresponding to a level of optical distortion (high to low) and select the suitable front face design adapted to the wearer parameters and particularly to the optical distortion sensitivity data of the wearer.

According to another example, wherein specific optical distortion sensitivity data are measured in the nasal and temporal parts of the lens, these measurements are used to customize the lens design, according to the specific optical distortion sensitivity data.

Figure 2:
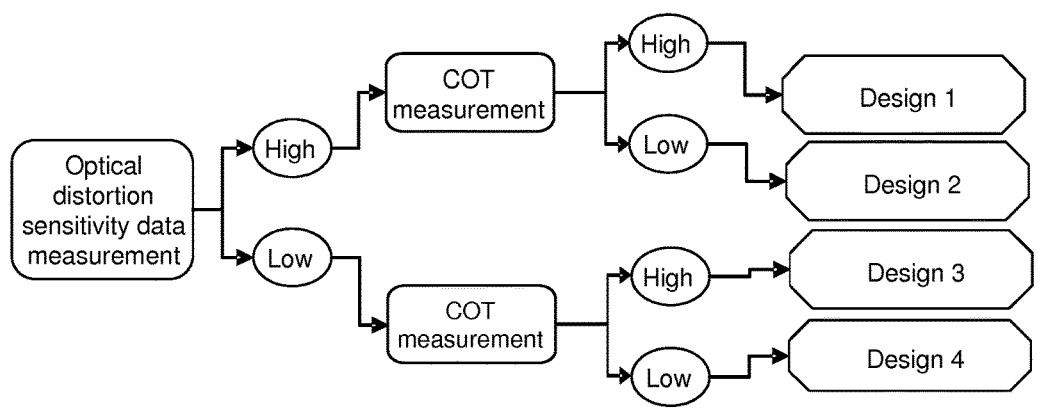
FIGS. 2 to 4 are illustrations of exemplary chart-flows of the determining step of the method illustrated in FIG. 1.
Figure 3:
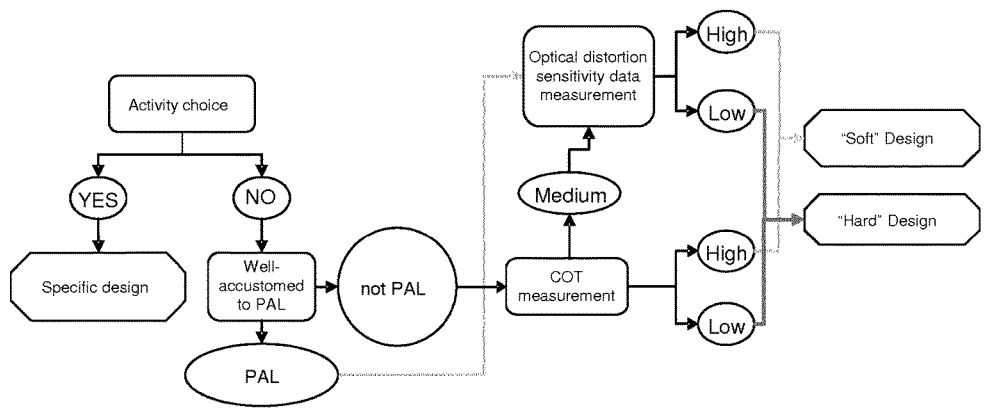
Figure 4:
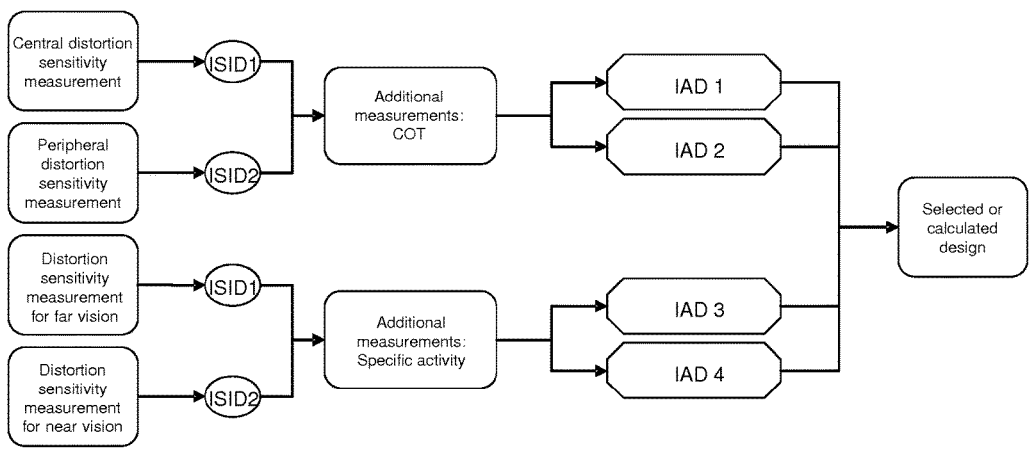

FIGS. 2 to 4 are illustrations of exemplary chart-flows of the determining step S6 of the method.

FIG. 2 illustrates a chart-flow of an exemplary of a lens design determining step wherein the lens design of the optical lens adapted to the wearer is determined based at least on optical distortion sensitivity data representative of the sensitivity of the wearer to optical distortions and on eye-head coefficient (COT) representative of the eye-head behavior of the wearer.

For example, designs 1 (the softest) to 4 (the hardest) correspond to an increasing level of optical distortions (low to high).

Another example is illustrated in FIG. 3. In this example, the lens design of the optical lens adapted to the wearer is determined based on several wearer parameters.

The determined lens design can depend on the activity of the wearer. In this case a specific lens design can be determined.

If the determined lens design does not depend on the activity, it can be based on the fact that the wearer is used to wearing lenses and especially progressive lenses and if the wearer is well-accustomed to the distortions of its initial equipment.

Indeed, a wearer well-accustomed to the distortions of his initial equipment comes to weight the intrinsic optical distortion sensitivity index.

Then, the lens design is determined based on the sensitivity of the wearer to optical distortions and on eye-head coefficient behavior of the wearer according to an embodiment of the invention.

The example illustrated in FIG. 4 relates to a lens design determining step wherein measurements of specific optical distortion sensitivity data are necessary in order to select or calculate a lens design best adapted to the wearer:
  in the central and peripheral parts of the field of vision associated with measurements of the eye-head behavior of the wearer, or
  in far vision and near vision associated with a specific activity of the wearer.

After determining a lens design of an optical lens adapted to a wearer according to the invention, an optical lens having the determined lens design can be manufactured according to a method of providing an optical lens adapted to a wearer according to the invention, by using traditional methods of manufacturing an optical lens from a given lens design, for example by free form surfacing of the front and rear surfaces in order to control the geometries of the two surfaces of the lens.

According to another aspect, the invention further relates to a lens design determining system adapted to implement a method for determining a lens design of an optical lens adapted to a wearer as previously described according to the invention.

The lens design determining system comprises receiving means adapted to receive wearer parameters, wherein the wearer parameters comprise at least optical distortion sensitivity data representative of the sensitivity of the wearer to optical distortion.

The wearer parameters can further comprise ophthalmic parameters relating to the ophthalmic requirements of the wearer.

Moreover, the lens design determining system comprises determining means adapted to determine the lens design of the optical lens adapted to the wearer based at least on the wearer parameters.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method, implemented by a computer, for determining a lens design of an optical lens adapted to a wearer, the method comprising:
   determining a lens design for the optical lens adapted to the wearer, based at least on wearer parameters, wherein
   the wearer parameters comprise at least optical distortion sensitivity data representative of sensitivity of the wearer to optical distortions due to the optical lens adapted to and newly worn by the wearer.

2. The method according to claim 1, wherein
   each optical distortion sensitivity data is compared to a scale to define an optical distortion sensitivity index.

3. The method according to claim 1, wherein
   the wearer parameters further comprise prescription data and ophthalmic parameters relating to ophthalmic requirements of the wearer.

4. The method according to claim 1, wherein
   the lens design is calculated based at least on the optical distortion sensitivity data.

5. The method according to claim 1, wherein
   the lens design is selected amongst a list of lens designs, the selection being based at least on the optical distortion sensitivity data.

6. The method according to claim 1, wherein
   the lens design comprises at least dioptric lens design.

7. The method according to claim 1, wherein
   the lens design comprises geometrical parameters of the optical lens.

8. The method according to claim 1, further comprising measuring the optical distortion sensitivity data of the wearer.

9. The method according to claim 8, wherein
   the optical distortion sensitivity data are measured upon a perception test or a discomfort measurement test carried out on the wearer.

10. The method according to claim 8, wherein
    during the optical distortion sensitivity data measurement, optical distortion patterns are presented to the wearer.

11. The method according to claim 10, wherein
    the optical distortion patterns comprise dynamic optical distortion patterns.

12. The method according to claim 8, wherein
    the optical distortion sensitivity data are measured in specific gazing directions.

13. The method according to claim 8, wherein
    the optical distortion sensitivity data are measured in at least a specific part of the field of vision.

14. A method of manufacturing an optical lens adapted for a wearer, comprising:
    determining a lens design for the optical lens according to claim 1; and
    manufacturing the optical lens having the determined lens design.

15. A lens design determining system for determining lens design adapted to a wearer, the system comprising:
    a computer processor configured to
       receive wearer parameters comprising at least optical distortion sensitivity data representative of sensitivity of the wearer to optical distortions due to the lens adapted to and newly worn by the wearer; and
       determine the lens design of the optical lens adapted to the wearer based at least on the wearer parameters.

16. A non-transitory computer readable medium comprising a computer program comprising one or more stored sequences of instructions that are accessible to a processor and which, when executed by the processor, cause the processor to perform:
    determining a lens design for an optical lens adapted to a wearer, based at least on wearer parameters, wherein
    the wearer parameters comprise at least optical distortion sensitivity data representative of sensitivity of the wearer to optical distortions due to the optical lens adapted to and newly worn by the wearer.

* * * * *